United States Patent [19]

McKinnie et al.

[11] Patent Number: 5,210,321

[45] Date of Patent: May 11, 1993

[54] DIPHENYL OXIDE BROMINATION PROCESS

[75] Inventors: Bonnie G. McKinnie; Mark A. Templeton, both of Magnolia, Ark.

[73] Assignee: Ethyl Corporation, Richmond, Va.

[21] Appl. No.: 766,662

[22] Filed: Sep. 25, 1991

Related U.S. Application Data

[63] Continuation-in-part of Ser. No. 506,334, Apr. 9, 1990, abandoned.

[51] Int. Cl.$^5$ .............................................. C07C 41/22
[52] U.S. Cl. ................................... 568/639; 568/637
[58] Field of Search ............................. 568/637, 639

[56] References Cited

U.S. PATENT DOCUMENTS

| | | | |
|---|---|---|---|
| 3,763,248 | 10/1973 | Mitchell | 260/649 |
| 4,717,776 | 1/1988 | Brackenridge et al. | 568/637 |
| 4,740,629 | 4/1988 | Brackenridge et al. | 568/637 |

Primary Examiner—Marianne M. Cintins
Assistant Examiner—Margaret J. Page
Attorney, Agent, or Firm—David E. LaRose

[57] ABSTRACT

A process for producing a mixture of brominated diphenyl oxides with an average bromine number of 7.0 to 7.8 is improved by the utilization of a multi-step, multi-catalyst procedure. The process uses a zirconium catalyst in the first reaction and an iron catalyst in the second reaction to yield a whiter flame retardant product having less tendency to discolor plastic resins.

12 Claims, No Drawings

DIPHENYL OXIDE BROMINATION PROCESS

This is a continuation-in-part of U.S. patent application Ser. No. 07/506,334 filed Apr. 9, 1990, now abandoned.

This invention relates to an improved process for making a mixture of brominated diphenyl oxides having an average of from about 7 to about 8 atoms of bromine per molecule of diphenyl oxide. The term "brominated diphenyl oxide" herein means arbrominated diphenyl oxide.

BACKGROUND

Certain brominated diphenyl oxide mixtures are sold and denominated by the flame retardant industry as octabromodiphenyl oxide. For the sake of simplicity, these mixtures will hereinafter be referred to as "Octabrom". Typically, the commercially significant Octabroms have an average bromine number of about 7 to about 7.8 and contain 0-2 weight percent pentabromodiphenyl oxide, 5-15 weight percent hexabromodiphenyl oxide, 40-55 weight percent heptabromodiphenyl oxide, 25-40 weight percent octabromodiphenyl oxide, 5-15 weight percent nonabromodiphenyl oxide, and 0-2 weight percent decabromodiphenyl oxide. As can be appreciated, for any particular Octabrom, the average number of bromine atoms per molecule of brominated diphenyl oxide, hereinafter referred to as the "average bromine number," is dependent upon the amounts and the identities of the particular bromo species which are present in the mixture. The "average bromine number" can be calculated by multiplying the weight percent of each bromo homolog by the number of bromine atoms in that homolog, adding the resulting products and dividing the sum by 100.

One process for making Octabrom, which is described in U.S. Pat. No. 3,965,197, uses an aluminum halide to catalyze the bromination of diphenyl oxide. Another process for making Octabrom is disclosed in U.S. Pat. No. 4,740,629. While both processes represent significant advances in the art, they produce Octabrom products which are often somewhat colored. In fact, most present day Octabrom processes do not produce the desired white product, but rather, produce a product which has a noticeable reddish color component.

In general, the prior art processes for preparing Octabrom utilize a reaction mass containing diphenyl oxide, catalyst and a substantial excess of bromine. By substantial excess of bromine is meant more than 25% excess based on the stoichiometric amount of bromine needed to achieve the desired average bromine number. As the bromination of the diphenyl oxide progresses, the bromine number of the product is monitored. When the analysis of the product in the reaction mass indicates that the desired bromine number is being approached, water is added to the reaction mass to "kill" the catalyst. However, since the reaction mass contains a substantial excess of bromine, it is very difficult to "kill" the catalyst at the precise time needed to consistently prepare a product having the desired average bromine number. There is a need therefore for a process which provides a product which consistently contains the desired average bromine number.

An acceptable standard for determining the color components of an Octabrom product is provided by the use of the Hunter color values "L", "a", and "b" which can be measured with a HunterLab Spectrocolorimeter. The "L" value is a measure of lightness versus darkness or clearness versus cloudiness, higher values having greater lightness or clearness. The "a" and "b" values are measures of color. Positive "a" values indicate redness, and negative "a" values indicate greenness. Positive "b" values indicate yellowness and negative "b" values indicate blueness. Octabrom typically has HunterLab "L" values of 80 to 86, "a" values of 1 to 50 and "b" values of 18 to 22 and can have a significant reddish tint when iron is used to catalyze the reaction. Because of the wide variation in "a" values, it is difficult to maintain consistent color in thermoplastic resin formulations which incorporate Octabrom as a flame retardant.

SUMMARY OF THE INVENTION

Consequently, this invention provides a process for preparing an Octabrom product having excellent color characteristics. The process comprises: forming a first reaction mass by adding diphenyl oxide to a reaction vessel containing bromine and a catalytic amount of zirconium catalyst, the amount of bromine providing a molar ratio of from about 7 to about 8.5 moles of bromine per mole of diphenyl oxide added; maintaining the first reaction mass for that period of time and at that temperature which are sufficient to yield a mixture of brominated diphenyl oxides having an average bromine number from about 5.8 to about 6.5; subsequently forming a second reaction mass by adding an iron catalyst to the first reaction mass, and if needed, additional bromine, to yield an average bromine number of from about 7.0 to about 7.8.

The Octabrom produced by the process of this invention has excellent color characteristics. When used as a flame retardant in ABS-based formulations, the Octabrom of this invention does not contribute a reddish tint to articles made from such formulations. Furthermore, this invention provides a means for obtaining Octabrom with the desired color characteristics more consistently.

DETAILED DESCRIPTION

To form the first reaction mass, the reactor is initially charged with bromine and a catalytic amount of zirconium catalyst. It has been found that, under the process conditions of this invention, the zirconium catalyst is most effective in catalyzing the production of a brominated diphenyl oxide mixture having an average bromine number no greater than about 6.5. Additional bromination is only achieved slowly.

The amount of bromine initially charged should at least be an amount sufficient to obtain the average bromine number sought for the mixture in the first reaction mass and sufficient to provide a stirrable reaction mass. Since an excess of bromine does not adversely affect the obtainment of the desired average bromine number and since bromine will be needed for the arbromination which occurs in the second reaction mass, it is convenient to simply charge the reactor initially with sufficient bromine to satisfy the bromine requirements for the first and second reaction masses. This is not to say, however, that it is impermissible to initially charge the reactor with bromine sufficient to satisfy the needs of the first reaction mass and to then secondly charge the reactor with more bromine to satisfy the needs of the second reaction mass. Indeed, in practicing the process of this invention it will, in most cases, be desirable to initially charge a theoretically sufficient amount of bromine for both reaction masses and to then, if necessary, add additional bromine when forming the second reaction mass. Such additional bromine may be needed to replace bromine which is often lost due to entrainment in the hydrogen bromine (HBr) vapors evolving from the reaction mass. Considering the entrainment of bromine in the HBr vapors, the amount of bromine initially charged is within the range of from about 6 to about 9 moles of bromine per mole of diphenyl oxide added. It is feature of this invention that the bromination reaction is performed in the substantial absence of solvent other than bromine.

If the amount of bromine initially charged is in excess of the amount needed to achieve the desired bromine number, care must be taken to insure that the free bromine remaining in the first reaction mass prior to forming the second reaction mass does not exceed the amount of bromine required to obtain this bromine number, as the iron catalyst used in forming the second reaction mass is capable of brominating the diphenyl oxide to the extent of the bromine available. Thus, if too much bromine is present the desired average bromine number could be exceeded. Furthermore, if the free bromine content before forming the second reaction mass is a large excess, i.e., greater than about 20 wt. %, then addition of the iron catalyst may lead to a violent reaction that cannot be contained.

The zirconium catalyst charged to the reactor may be zirconium metal or a zirconium halide catalyst, including zirconium bromide, zirconium chloride, zirconium fluoride, or a mixture of any two or more of the foregoing. Preferably the zirconium catalyst charged is a zirconium halide catalyst and most preferably is zirconium tetrachloride ($ZrCl_4$).

The amount of zirconium tetrachloride catalyst charged is typically in the range of from about 0.05 wt.% to about 20 wt.% based on the weight of diphenyl oxide added to the reactor. Most preferably, the catalyst charged is from about 1 wt.% to about 8 wt.% based on the weight of the diphenyl oxide. The $ZrCl_4$ catalyst is familiar to those skilled in the art and is readily available from a number of sources.

The bromine and zirconium halide catalyst can be charged to the reactor together or separately, and, if charged separately, they can be charged in any order.

The diphenyl oxide which is fed to the charged reactor should be fed as quickly as possible, while adhering to the first reaction mass temperature requirement and the ability to safely handle the quantity of HBr evolving from the first reaction mass. In actual practice, the diphenyl oxide may be fed to the charged reactor vessel over a period of from about 30 minutes to about 20 hours or longer. The period of time for feeding the diphenyl oxide is a function of the batch size and the equipment limitations.

The reactor contents should be kept at a temperature within the range of from about 10° C. to about 90° C. and preferably from about 40° C. to about 70° C. during the diphenyl oxide addition. It is most preferable to hold the first reaction mass at reflux. In some instances it will be necessary to maintain sub- or super-atmospheric pressure to achieve reflux at the selected temperature.

The diphenyl oxide may be added as a solid or as a liquid melt. For ease of operation the diphenyl oxide is preferably added in molten form. Since diphenyl oxide melts at about 28° C., the temperature of the diphenyl oxide is preferably maintained above about 28° C. and most preferably about 30° to about 40° C. to prevent freeze-up in the feed conduit.

After the diphenyl oxide addition has been completed, the first reaction mass is maintained under the above-mentioned conditions until bromination substantially ceases. The substantial cessation of the bromination reaction is easily determined by the cessation or the near cessation of HBr evolution from the first reaction mass. When the bromination reaction has ceased, the brominated diphenyl oxide in the reaction mass will have an average bromine number of from about 5.8 to about 6.5.

Subsequent to attaining a bromine number of about 6 in the first reaction mass, a second reaction mass is formed by adding an iron catalyst to the first reaction mass, and if needed, additional amounts of bromine. The addition of the iron catalyst revives or speeds the bromination reaction.

The iron catalyst may be added all at once, or in small quantities. The rate at which the iron catalyst can be added is dependent on the ability to maintain the desired pressures and temperatures of the second reaction mass during the iron addition. Preferably, the iron catalyst is added as quickly as possible, considering maintenance of the second reaction mass temperature requirement and the ability to safely handle the quantity of HBr evolving from the second reaction mass. The temperature of the second reaction mass should be kept within the range of from about 20° C. to about 150° C. and preferably from about 50° C. to about 100° C. during the iron catalyst addition. Once all of the iron catalyst and additional bromine, if needed, have been added to form the second reaction mass, it is preferably held at a temperature of from about 100° C. to about 130° C. for 1 to 2 hours, or for such period of time as is necessary to obtain the desired average bromine number.

The iron catalyst added to the second reaction mass may be metallic iron or an iron halide catalyst. When an iron halide catalyst is used, the catalyst may be an iron chloride, an iron bromide, an iron iodide, or an iron fluoride catalyst. When a metallic iron catalyst is used, the iron catalyst may be in the form of shavings, flakes, rings, saddles, beads, chunks, powder, and the like. In the most preferred embodiment, the iron catalyst is in the form of iron powder. The amount of iron catalyst used is dependent o the number of moles of diphenyl oxide present in the second reaction mass. It is preferable to use about 0.002 to about 0.15 mole of iron per mole of diphenyl oxide, and most preferably about 0.02 to about 0.035 moles of iron, per mole of diphenyl oxide.

If additional bromine is required to be added to the second reaction mass, it may be added before, after or during the addition of the iron catalyst. It is most desirable to add the bromine, if needed, after adding the iron catalyst in order to more easily control the heat of reaction.

Once a sample drawn from the second reaction mass indicates that the desired bromine number has been obtained, any further ar-bromination may be prevented by addition of water to the second reaction mass. Since only enough bromine is present, either initially or by subsequent addition, to obtain the desired bromine number, the use of water to prevent any further arbromination of the diphenyl oxide is not required. However, since water is also used in the purification of the product, the addition to the second reaction mass once the desired bromine number is obtained is a desirable practice.

The final brominated diphenyl oxide product can be recovered from the second reaction mass and purified by any of several conventional methods. For example, steam can be introduced into the second reaction mass to heat the mass to distill any remaining bromine therefrom and to form an aqueous mix. After the bromine has been removed, sodium carbonate is added to neutralize any acid that may be in the mix. Removal of catalyst from the neutralized aqueous mix is achieved by the addition of sodium gluconate or ethylenediaminetetraacetic acid tetrasodium salt ($Na_4EDTA$) which aids in the solubilization of the catalyst in the aqueous mix. Next toluene or another organic solvent is added along with additional water to form an aqueous phase and an organic phase. The organic and aqueous phases are separated and the organic phase is distilled or stripped of the toluene or organic solvent. Once these are removed from the mixture, the Octabrom product can be cooled until solidified and then broken or ground to the desired particle size.

The manner in which the process can be conducted is illustrated in the following Examples:

EXAMPLE I

In a one liter 4-neck round-bottom flask equipped with a mechanical stirrer, addition funnel, refrigerated condenser, and thermometer was placed about 697 grams of bromine and 2 grms of $ZrCl_4$. Diphenyl oxide (100 grams) was added dropwise over a period of two hours, and the vessel was maintained at 40° to 60° C. during the addition of the diphenyl oxide. The vessel was held at 60° C. for 20 minutes. A sample taken at the end of this period showed an average bromine number of 5.7. Iron powder (0.6 gram) was then added to the reaction mass. The reaction mixture was headed to 80° to 90° C. over a period of 30 minutes. Over the next 3 hours and 30 minutes, 30 mL of bromine was added in 5 mL portions as the temperature was increased to 110° to 115° C. The temperature was held at 110° to 115° C. for 1 hour and 20 minutes, then water was added to the vessel, the condenser set for distillation, and bromine distilled until the temperature was 115° C. to 120° C. Sodium gluconate (6 grams) and sodium carbonate (12 grams) were added followed by 175 mL toluene and 100 mL water. After stirring well, the organic layer was separated and washed well with hot water. The toluene solvent was removed under vacuum, leaving the brominated product.

To determine the Hunter values, the product Octabrom was dissolved in toluene such that a mixture of approximately 50 wt.% Octabrom and 50% wt.% toluene was obtained. The dissolved product was then placed in a 50 mm cell of a HunterLab Labscan model spectrocolorimeter. Samples with "a" values higher than about 5 are considered less desirable since they have a reddish color which can be imparted to thermoplastic resin formulations of which they are a part.

As measured by gas chromatography (GC), the product species distribution was as follows:

| Sample 1 | |
|---|---|
| Product Species | GC Area % |
| $Br_6$ | 15.3 |
| $Br_7$ | 46.6 |
| $Br_8$ | 26.1 |

-continued

| Sample 1 | |
|---|---|
| Product Species | GC Area % |
| $Br_9$ | 10.7 |
| $Br_{10}$ | 1.2 |

Based on the above area percents, the average bromine number was calculated to be 7.35.

Hunter values were as follows:

Hunter Values

L=96.0
a=−0.7
b=10.6

EXAMPLE II

In a one liter 4-neck round-bottom flask equipped with a mechanical stirrer, addition funnel, refrigerated condenser, and thermometer was placed about 686 grams of bromine and 1.4 grams of $ZrCl_4$. Diphenyl oxide (91 grams) was added dropwise over a period of one and one-half hours, and the vessel was maintained at 40° to 60° C. during the addition of the diphenyl oxide. The vessel was held at 82° C. for 15 minutes. A sample taken at the end of this period showed an average bromine number of 6.2. After an additional 1 hour and 10 minutes, iron powder (0.4 gram) was added to the reaction mass. The reaction mixture was heated from 75° to 115° C. over a period of 2 hours and 30 minutes. Bromine (13 mL) was added and the temperature was held at 110° to 115° C. for 1 hour and 20 minutes, then 20 mL water was added to the product, the condenser set for distillation, and bromine distilled until the temperature was 110° C. Sodium gluconate (4 grams) and sodium carbonate (8 grams) were added followed by 150 mL toluene and 100 mL water. After stirring well, the organic layer was separated and washed well with hot water. The toluene solvent was removed under vacuum leaving the brominated product. Product analysis was as follows:

| Sample 2 | |
|---|---|
| Product Species | GC Area % |
| $Br_6$ | 12.6 |
| $Br_7$ | 49.8 |
| $Br_8$ | 26.6 |
| $Br_9$ | 10.0 |
| $Br_{10}$ | 0.92 |

Based on the above area percents, the average bromine number was calculated to be 7.36.

Hunter values were as follows:

Hunter Values

L=87.0
a=1.7
b=19.7

EXAMPLE III

In a one liter 4-neck round-bottom flask equipped with a mechanical stirrer, addition funnel, refrigerated condenser, and thermometer was placed about 660 grams of bromine and 1.8 grams of $ZrCl_4$. Diphenyl oxide (91 grams) was added dropwise over a period of two hours, and the vessel was maintained at 50° to 60° C. during the addition of the diphenyl oxide. The vessel was held at 70-74° C. for one hour. A sample taken at the end of this period showed an average bromine number of 5.97. Iron powder (0.3 gram) was then added to the reaction mass. The reaction mixture was heated to 95° C. over a period of 1 hour and 30 minutes. Bromine (6 mL) was added and the temperature was increased to 110° C. The temperature was held at 110° to 115° C. overnight, then another 18 mL of bromine was added over a period of 3 hours and 15 minutes while the temperature was maintained at 110° C. One hour and 15 minutes later, 20 mL water was added to the product, the condenser set for distillation, and bromine distilled until the temperature was 110° C. Sodium gluconate (4 grams) and sodium carbonate (8 grams) were added followed by 150 mL toluene and 100 mL water. After stirring well, the organic layer was separated and washed well with hot water. The toluene solvent was removed under vacuum leaving the brominated product.

| Sample 3 | |
|---|---|
| Product Species | GC Area % |
| $Br_6$ | 14.7 |
| $Br_7$ | 46.7 |
| $Br_8$ | 27.4 |
| $Br_9$ | 10.2 |
| $Br_{10}$ | 1.0 |

Based on the above area percents, the average bromine number was calculated to be 7.36.

Hunter values were as follows:

Hunter Values

L=93.5
a=−0.1
b=14.1

The product produced as a result of this invention was water white or yellowish in solution rather than reddish or brown as with other processes. Typical Octabrom product made by previous processes has average Hunter "a", "b" and "L" values of 5.75, 20.3, and 85.

The mixtures of brominated diphenyl oxides having average bromine numbers between 7.0 and 7.8 are useful as flame retardants in a wide variety of organic materials such as polyethylene, polypropylene, polyesters, acrylonitrilebutadienestyrene terpolymer, styrene, high impact polystyrene, styrenebutadiene copolymer, styrene-maleic anhydride copolymer, polyphenylene ethers and blends of the above. The amount used is generally an amount to provide about 5-15 weight percent bromine based on the polymer. Synergists, such as antimony oxide, are routinely included.

It will be evident that variations in the process are possible within the spirit and scope of the appended claims.

What is claimed is:

1. A process for preparing a mixture of brominated diphenyl oxides having improved color characteristics, said process comprising:
   (a) forming a first reaction mass by adding molten diphenyl oxide to a reaction vessel containing bromine and a catalytic amount of zirconium catalyst, the amount of bromine providing a molar ratio of from about 7 to about 8.5 moles of bromine per mole of diphenyl oxide added;
   (b) maintaining the first reaction mass for a period of time and at a temperature which are sufficient to yield a mixture of brominated diphenyl oxides having an average bromine number of from about 5.8 to abut 6.5; and
   (c) subsequent to the substantial cessation of the bromination reaction in he first reaction mass, forming a second reaction mass by adding an iron catalyst to the first reaction mass, and if needed, additional amounts of bromine, to yield a mixture of brominated diphenyl oxides having improved color characteristics and processing an average bromine number of from about 7.0 to about 7.8.

2. The process of claim 1 being conducted in the substantial absence of a solvent other than liquid bromine.

3. The process of claim 1 wherein the temperature of the first reaction mass during (a) and (b) is from about 10° C. up to reflux.

4. The process of claim 1 wherein the diphenyl oxide is added to the reaction vessel over a period of about 30 minutes to about 20 hours.

5. The process of claim 1 wherein the zirconium catalyst is a zirconium halide catalyst.

6. The process of claim 5 wherein the zirconium halide catalyst is charged to the reaction vessel as zirconium chloride.

7. The process of claim 1 wherein the iron catalyst is an iron powder catalyst.

8. The process of claim 1 wherein the temperature in step (c) is maintained in a range of from about 100° C. to about 130° C.

9. A process for preparing an Octabrom with improved color characteristics, said process comprising:
   (a) forming a first reaction mass by adding diphenyl oxide to reaction vessel previously charged with bromine and a catalytic amount of zirconium catalyst, the amount of bromine providing a molar ratio of from about 7 to about 8.5 moles of bromine per mole of diphenyl oxide added;
   (b) maintaining the first reaction mass for a period of time and at a temperature ranging from abut b 10° C. to reflux, such that a mixture of brominated diphenyl oxides is formed, said mixture having an average of about 6.0 to about 6.5 arbromine atoms per molecule of diphenyl oxide added in (a);
   (c) subsequent to the substantial cessation of the bromination reaction in the first reaction mass, forming a second reaction mass by adding an iron powder catalyst to the first reaction mass, and if needed, additional amounts of bromine to yield Octabrom having improved color characteristics; and
   (d) recovering Octabrom having improved color characteristics from the second reaction mass.

10. The process of claim 9 conducted in the substantial absence of a solvent other than liquid bromine.

11. The process of claim 10 wherein the diphenyl oxide is added to the reaction vessel over a period of about 30 minutes to about 10 hours.

12. The process of claim 9 wherein the temperature in step (c) is maintained in a range of about 70° C. to about 150° C.

* * * * *